US010215755B2

(12) United States Patent
Lerner et al.

(10) Patent No.: US 10,215,755 B2
(45) Date of Patent: Feb. 26, 2019

(54) METHOD OF DIAGNOSING AND TREATING EPSTEIN BARR VIRUS-BASED MYALGIC ENCEPHALOMYELITIS CHRONIC FATIGUE SYNDROME PATIENTS

(71) Applicants: CFS, LLC, Beverly Hills, MI (US); Ohio State University, Columbus, OH (US)

(72) Inventors: A. Martin Lerner, Birmingham, MI (US); Ronald M. Glaser, Dayton, OH (US)

(73) Assignees: CFS, LLC, Beverly Hills, MI (US); OHIO STATE UNIVERSITY, Columbus, OH (US)

( * ) Notice: Subject to any disclaimer, the term of this patent is extended or adjusted under 35 U.S.C. 154(b) by 0 days.

(21) Appl. No.: 14/926,989

(22) Filed: Oct. 29, 2015

(65) Prior Publication Data
US 2017/0146534 A1 May 25, 2017

Related U.S. Application Data

(62) Division of application No. 13/645,123, filed on Oct. 4, 2012, now abandoned.

(51) Int. Cl.
| G01N 33/569 | (2006.01) |
| A61K 31/522 | (2006.01) |
| A61K 31/52 | (2006.01) |
| A61K 31/662 | (2006.01) |
| A61K 31/7056 | (2006.01) |

(52) U.S. Cl.
CPC ....... *G01N 33/56994* (2013.01); *A61K 31/52* (2013.01); *A61K 31/522* (2013.01); *A61K 31/662* (2013.01); *A61K 31/7056* (2013.01); *G01N 2333/05* (2013.01); *Y02A 50/401* (2018.01); *Y02A 50/402* (2018.01); *Y02A 50/57* (2018.01)

(58) Field of Classification Search
None
See application file for complete search history.

(56) References Cited

U.S. PATENT DOCUMENTS

| 3,267,934 A | 8/1966 | Thornton |
| 3,572,321 A | 3/1971 | Bloomfield et al. |
| 3,595,218 A | 7/1971 | Kirkpatrick et al. |
| 3,605,727 A | 9/1971 | Zenevich et al. |
| 3,829,766 A | 8/1974 | Herz |
| 3,858,034 A | 12/1974 | Anderson |
| 3,868,567 A | 2/1975 | Ekstrom |
| 4,183,354 A | 1/1980 | Sibley et al. |
| 4,275,742 A | 6/1981 | Faisandier |
| 4,457,315 A | 7/1984 | Bennish |
| 4,457,731 A | 7/1984 | Patrickson et al. |
| 4,493,328 A | 1/1985 | Saito |
| 4,544,634 A | 10/1985 | Krenitsky |
| 4,546,776 A | 10/1985 | Bellin et al. |
| 4,583,553 A | 4/1986 | Shah et al. |
| 4,622,980 A | 11/1986 | Kunig |
| 4,695,570 A | 9/1987 | Krenitsky |
| 4,784,153 A | 11/1988 | Marks |
| 4,854,327 A | 8/1989 | Kunig |
| 4,883,065 A | 11/1989 | Kelen |
| 4,897,394 A | 1/1990 | Zimmerman et al. |
| 4,957,924 A | 9/1990 | Beauchamp |
| 4,987,901 A | 1/1991 | Kunig |
| 5,033,475 A | 7/1991 | Ueda et al. |
| 5,055,296 A | 10/1991 | Wagle et al. |
| 5,061,708 A | 10/1991 | Krenitsky |
| 5,079,252 A | 1/1992 | Beauchamp |
| 5,189,022 A | 2/1993 | Bridge et al. |
| 5,197,480 A | 3/1993 | Gebhardt |
| 5,206,008 A | 4/1993 | Loria |
| 5,206,248 A | 4/1993 | Smith |
| 5,213,106 A | 5/1993 | Lerner |
| 5,267,570 A | 12/1993 | Preston |
| 5,298,019 A | 3/1994 | Borodic |
| 5,312,817 A | 5/1994 | Snorrason |
| 5,357,968 A | 10/1994 | Lerner |
| 5,405,850 A | 4/1995 | Blumenkopf |
| 5,426,020 A | 6/1995 | Bagchi et al. |
| 5,426,028 A | 6/1995 | Levy et al. |
| 5,461,042 A | 10/1995 | Loria |
| 5,464,020 A | 11/1995 | Lerner |
| 5,491,150 A | 2/1996 | Aoki et al. |

(Continued)

OTHER PUBLICATIONS

Sommer, 1996, Journal of General Virology, vol. 77, p. 2795-2805.*
Jones et al. (JAMA, 1988, vol. 148, p. 1957-1960, Abstract only).*
Glaser et al. (Brain, Behavior and Immunity, 2005, p. 91-103).*
Martins et al. (Immunopathology, 2008, p. 34-41).*
Marin, et al., Modification of Muscle Activity after BOTOX Injections in Spasmodic Torticollis Annals of Neurology, vol. 32, No. 3, Sep. 1992, pp. 411-412.
Griffiths, et al., Molecular Biology and Immunology of Cytomegalovirus, Biochem. J., (1987) vol. 241, pp. 313-324.
Lin, et al., Prolonged Inhibitory Effect of 9-(1,3-Dihydroxy-2-Propoxymethyl)Guanine Against Replication of Epstein-Barr Virus, Journal of Virology, Apr. 1984, vol. 50, No. 1, pp. 50-55.

(Continued)

*Primary Examiner* — Agnieszka Boesen
(74) *Attorney, Agent, or Firm* — Brooks Kushman P.C.

(57) ABSTRACT

A method of diagnosing a subset of Epstein Barr Virus, Myalgic Encephalomyelitis Chronic Fatigue Syndrome (ME/CFS) patients through a multi-prong clinical/serological analysis is provided wherein Epstein Barr Virus Abortive Lytic Replication (EBV) is determined as the specific causal agent through the use of serum antibodies to EBV encoded dUTPase and serum antibodies to EBV DNA Polymerase as molecular markers. A method of treating patients diagnosed with Epstein Barr Virus Abortive Lytic Replication (EBV), Myalgic Encephalomyelitis Chronic Fatigue Syndrome (ME/CFS) with specific antiviral nucleosides is also provided, to alleviate the condition.

15 Claims, 1 Drawing Sheet

(56) References Cited

U.S. PATENT DOCUMENTS

| | | |
|---|---|---|
| 5,538,856 A | 7/1996 | Levy et al. |
| 5,545,550 A | 8/1996 | Grossberg et al. |
| 5,545,670 A | 8/1996 | Bissbort et al. |
| 5,872,123 A | 2/1999 | Lerner |
| 6,258,818 B1 | 7/2001 | Lerner |
| 6,506,553 B1 * | 1/2003 | Smith .................. C07K 14/005 424/184.1 |

OTHER PUBLICATIONS

Lerner, et al., Repetitively Negative Changing T Waves at 24-h Electrocardiographic Monitors in Patients with the Chronic Fatigue Syndrome, Chest vol. 104, No. 5, Nov. 1993, pp. 1417-1421; Abstract only.

Sinclair, et al., Repression of Human Cytomegalovirus Major Immediate Early Gene Expression in a Monocytic Cell Line, Journal of General Virology (1992) vol. 73, pp. 433-435; Abstract only.

Braun, et al., Selective Peripheral Denervation for Spasmodic Torticollis: Is the Outcome Predictable?, J. Neurol (1995) 242(8):504-507.

Braun, et al., Selective Peripheral Denervation for the Treatment of Spasmodic Torticollis V., Neurosurgery, vol. 35, No. 1, Jul. 1994, pp. 58-63.

Gow, et al., Studies on Enterovirus in Patients with Chronic Fatigue Syndrome, Clinical Infectious Diseases, 1994; 18 (Suppl. 1), pp. S126-S129; Abstract only.

Ablashi, Dharam V., Summary: Viral Studies of Chronic Fatigue Syndrome, Clinical Infectious Diseases, 1994:18 (Suppl. 1), pp. S130-S133.

Fukuda, et al., The Chronic Fatigue Syndrome: A Comprehensive Approach to Its Definition and Study, Annals of Internal Medicine, 1994, vol. 121, No. 12, pp. 953-959; Abstract only.

Swartz, Morton N., The Chronic Fatigue Syndrome—One Entity or Many?, The New England Journal of Medicine, vol. 319, No. 26, 1988, pp. 1726-1728; Abstract only.

Yao, Q.Y., The Epstein-Barr Virus: Host Balance in Acute Infectious Mononucleosis Patients Receiving Acyclovir Anti-Viral Therapy, Int. J. Cancer, 1989, vol. 43, pp. 61-66; Abstract only.

Bou-Holaigah, et al., The Relationship Between Neurally Mediated Hypotension and the Chronic Fatigue Syndrome, Journal of the American Medical Association, vol. 274, No. 12, pp. 961-967; Abstract only.

Valacyclovir HC1 (VALTREX) Provides Simplified Dosing and Increased Efficacy in the Treatment of Herpes Virus Infections Int. Pharm. Abstr. 1994; 31:2244-5. Abstract No. 3111836.

Valcyte tm. (valganciclovir hydrochloride tablets), pamphlet published and distributed by Roche Pharmaceuticals, Roche Laboratories, Inc., Nutley, NJ 07110, issued Mar. 2001.

Klein, George, Viral Latency and Transformation: The Strategy of Epstein-Barr Virus, Cell, 1989, vol. 58, pp. 5-8; Abstract only.

Jones et al.; Antibodies to Epstein-Barr Virus-Specific DNase and DNA Polymerase in the Chronic Fatigue Syndrome; Arch Intern Med—vol. 147 Sep. 1988; 4 pages.

Natelson et al; High Titers of Anti-Epstein-Bar Virus DNA Polymerase are Found in Patients with Severe Fatiguing Illness; Journal of Medical Virology 42:42-46 Apr. 6, 1993; 5 pages.

Liu et al.; Antibody Against Epstein-Barr Virus DNA Polymerase Activity in Sera of Patients With Nasopharyngeal Carcinoma; Journal of Medical Virology 48: 101-105 A Jan. 16, 1989; 5 pages.

Dittmer, et al., Multiple pathways for Epstein-Barr virus episome loss from nasopharyngeal carcinoma; Int J Cancer: Nov. 1, 2008; 123(9): 2105-2112.

Waldman, et al., Epstein-Barr virus-encoded dUTPase enhances proinflammatory cytokine production by macrophages in contact with endothelial cells: Evidence for depression-induced atherosclerotic risk; Brain Behav. Immun. Feb. 2008; 22(2): 215-223.

Ariza, et al., The EBV-Encoded dUTPase Activates NF-kB through the TLR2 and MyD88-Dependent Signaling Pathway, J Immunol 2009; 182: 851-859; http://www.jimmunol.org/content/182/2/851.

Stowe, et al., Chronic herpesvirus reactivation occurs in aging; Experimental Gerontology 42 (2007) 563-570; www.elsevier.com/locate/expgero.

Yang, et al., Glucocorticoids activate Epstein Barr virus lytic replication through the upregulation of immediate early BZLF1 gene expression; Brain, Behavior, and Immunity 24 (2010) 1089-1096.

Lin et al., Prolonged inhibitory effect of 9-(1,2-dihydroxy-2-propoxymethyl)guanine against replication of Epstein-Barr virus; Journal of Virology; Apr. 1984, vol. 50, No. 1, pp. 50-55; Abstract only.

Binkley, et al., Evidence for the Role of Epstein Barr Virus Infections in the Pathogenesis of Acute Coronary Events, PLOS ONE; Jan. 2013, vol. 8, Issue 1, e54008, pp. 1-6.

Jones, et al., Antibodies to Epstein-Barr Virus-Specific DNase and DNA Polymerase in the Chronic Fatigue Syndrome, 1988, vol. 148, pp. 1957-1960, Abstract Only.

Lerner, et al., Antibody to Epstein-Barr Virus Deoxyuridine Triphosphate Nucleotidohydrolase and Deoxyribonucleotide Polymerase in a Chronic Fatigue Syndrome Subset, Nov. 2012, vol. 7, pp. 1-7

Sashihara, et al., Human Antibody Titers to Epstein-Barr Virus (EBV) gp350 Correlate with Neutralization of Infectivity Better than Antibody Titers to EBV gp42 Using a Rapid Flow Cytometry-Based EBC Neutralization Assay, Virology, 2009, vol. 391, pp. 249-256.

Sommer, et al., Cloning and expression of the Epstein-Barr Virus-encoded dUTPase: patients with acute, reactivated or chronic virus infection develop antibodies against the enzyme, Journal of General Virology, 1996, vol. 77, pp. 2795-2805.

Wong, et al., Rapid Detection of Antibodies in Sera Using Multiplexed Self-Assembling Bead Arrays, J. Immunol. Methods, 2009, vol. 31, pp. 171-182.

Holmes, et al, A Cluster of Patients with a Chronic Mononucleosis-Like Syndrome: Is Epstein-Barr Virus the Cause? Journal of the American Medical Association, 1987, vol. 257, No. 17, pp. 2297-2302; Abstract only.

Peterson, et al, A Controlled Trial of Intravenous Immunoglobulin G in Chronic Fatigue Syndrome, The American Journal of Medicine, 1990, vol. 89, pp. 554-560; Abstract only.

Lloyd, et al, A Double-Blind, Placebo-Controlled Trial of Intravenous Immunoglobulin Therapy in Patients with chronic Fatigue Syndrome, The American Journal of Medicine, 1990, vol. 89, pp. 561-568; Abstract only.

Lerner, et al., A New Cardiomyopathy: A Pilot Study of Intravenous Ganciclovir in a Subset of the Chronic Fatigue Syndrome, Depts. of Medicine, Wm. Beaumont Hospital, Wayne State Univ., Sch. of Med., Royal Oak, MI 1997 6:110-117.

Lerner, et al., A Preliminary 6 Month Trial of Valacyclovir (VAL) in Chronic Fatigue Syndrome (CFS) Using the Epstein-Barr Virus (EBV), Cytomegalovirus (HCMV) Paradigm, Abstract for 36.sup.th Annual Meeting of the Infectious Disease Society of America; Abstract only.

Lerner, et al., A Preliminary Randomized Double-Blinded Controlled Six Month Trial of Valacyclovir in Chronic Fatigue Syndrome Using the Epstein-Barr Virus/Cytomegalovirus Paradigm, 36.sup.th Annual Meeting of the Infectious Diseases Society of America, Nov. 13-15, 1998, Denver, CO.

Sixbey et al., A Second Site for Epstein-Barr Virus Shedding: The Uterine Cervix, The Lancet, Nov. 1986, pp. 1122-1124; Abstract only.

Dworkin, et al., Abnormal Left Ventricular Myocardial Dynamics in Eleven Patients with Chronic Fatigue Syndrome, Clinical Nuclear Medicine, Aug. 1994, vol. 19, No. 8, pp. 675-677; Abstract only.

Straus, et al., Acyclovir Treatment of the Chronic Fatigue Syndrome, The New England Journal of Medicine, vol. 319, No. 26, pp. 1692-1698; Abstract only.

Borodic, et al., Botulinum a Toxin for Spasmodic Torticollis: Multiple vs. Single Injection Points per Muscle, Head & Neck, 14(1):33-7, Jan.-Feb. 1992; Abstract only.

(56) References Cited

OTHER PUBLICATIONS

Brown, et al., Pharmacokinetics of Valganciclovir and Ganciclovir Following Multiple Oral Dosage of Valganciclovir in HIV-and CMV-Seropositive Volunteers, Adis International Limited; Clin Pharmacokinet Aug. 1999: 37 (2), 167-176.
Montague, Terrence J., Cardiac Effects of Common Viral Illnesses; Chest Magazine, Nov. 1988; nol. 94, No. 5 pp. 919-925—article and commentary.
Schooley, et al., Chronic Epstein-Barr Virus Infection Associated with Fever and Interstitial Pneumonitis, Annals of Internal Medicine, 1986, vol. 104, pp. 636-643; Abstract only.
Holmes, et al., Chronic Fatigue Syndrome: A Working Case Definition, Annals of Internal Medicine, 1988, vol. 108, pp. 387-389.
Deuschl, et al., Clinical and Polymographic Investigation of Spasmodic Torticollis, Journal of Neurology, vol. 239, pp. 9-15 (1992).
Klemola, et al., Cytomegalovirus as a Possible Cause of a Disease Resembling Infectious Mononucleosis, British Medical Journal, 1995, vol. 2, pp. 1099-1102.
Boghen, et al., Effectiveness of Botulinum Toxin in the Treatment of Spasmodic Torticollis, European Neurology, 33 (3):199-203, 1993.
Sumaya, et al., Enhanced Serological and Virological Findings of Epstein-Barr Virus in Patients with AIDS and AIDS-Related Complex, The Journal of Infectious Diseases, 1986, vol. 154, No. 5, pp. 864-870; Abstract only.
Sixbey, et al., Epstein-Barr Virus Replication in Oropharyngeal Epithelial Cells, The New England Journal of Medicine, vol. 310, No. 19, 1984, pp. 1225-1230.; Abstract only.
Henle, et al., Epstein-Barr Virus-Specific IgA Serum Antibodies as an Outstanding Feature of Nasopharyngeal Carcinoma, Int. J. Cancer, 1976, vol. 17, pp. 1-7; Abstract only.
Fields Virology 3rd Edition. Field et al Eds. Lippincott-Racen, Phil. Pa, 1995, pp. 2834-2835.
Buchwald, et al., Frequency of 'Chronic Active Epstein-Barr Virus Infection' in a General Medical Practice, Journal of the American Medical Association, 1987, vol. 257, No. 17, pp. 2303-2307; Abstract only.

Whitley, et al., Herpes Simplex Encephalitis-Vidarabine Therapy and Diagnostic Problems, The New England Journal of Medicine, Feb. 5, 1981; vol. 304, No. 6, pp. 313-318.; Abstract only.
Leach, Charles T., Human Herpes Virus-6: Clinical Implications of a Recently Discovered Ubiquitous Agent, The Journal of Pediatrics, 1992, vol. 121, No. 2, pp. 173-181; Abstract only.
Nikoskelainen, et al., IgM Antibodies Specific for Epstein-Barr Virus in Infectious Mononucleosis Without Heterophil Antibodies, British Medical Journal, 1974, vol. 4, pp. 72-75.
Moss, et al., Immune Surveillance Against Epstein-Barr Virus, Immunology, vol. 4, 1992, pp. 97-104; Abstract only.
Wu, et al., In Situ Detection of Human Cytomegalovirus Immediately-Early Gene Transcripts, etc. AIDS, 1992, vol. 6, No. 8, pp. 777-785; Abstract only.
Niederman, et al., Infectious Mononucleosis, Journal of the American Medical Association, 1968, vol. 203, No. 3, pp. 205-209; Abstract only.
Rowe, et al., Is Neurally Mediated Hypotension an Unrecognized Cause of Chronic Fatigue?, The Lancet, Mar. 11, 1995, vol. 345, Issue 8950, pp. 623-624; Abstract only.
Jung, et al.; Single-Dose Pharmacokinetics and Valganciclovir in HIV- and CMV-Seropositive Subjects, Pharmacokinetics and Pharmacodynamics, J. Clin Pharmacol 1999; 39:800-804.
Heneine, et al., Lack of Evidence for Infection with Known Human and Animal Retroviruses in Patients with Chronic Fatigue Syndrome, Clinical Infectious Diseases 1994; 18 (Suppl. 1), pp. S121-S125; Abstract only.
Lerner, et al; IgM Serum Antibodies to Human Cytomegalovirus Nonstructural Gene Product p52 and CM.sub.3 (UL44 and UL57) Are Uniquely Present in a subset of Patients with Chronic Fatigue Syndrome, in vivo 16: 153-160 (2002).
Lerner, et al; A Small Randomized Placebo-Controlled Trial of the use of Antiviral Therapy for Patients with Chronic Fatigue Syndrome, Clinical Infectious Diseases 2001, vol. 32, pp. 1657-1658.
Golden, et al., Leukocyte-Transforming Agent: Prolonged Excretion by Patients with Mononucleosis and Excretion by Normal Individuals, The Journal of Infectious Diseases, 1973, vol. 127, No. 4, pp. 471-473; Abstract only.
Southern, et al., Medical Consequences of Persistent Viral Infection, New England Journal of Medicine, vol. 314, No. 6, pp. 359-367; Abstract only.

\* cited by examiner

ME/CFS Treatment Decision Tree

ME/CFS Treatment Decision Tree

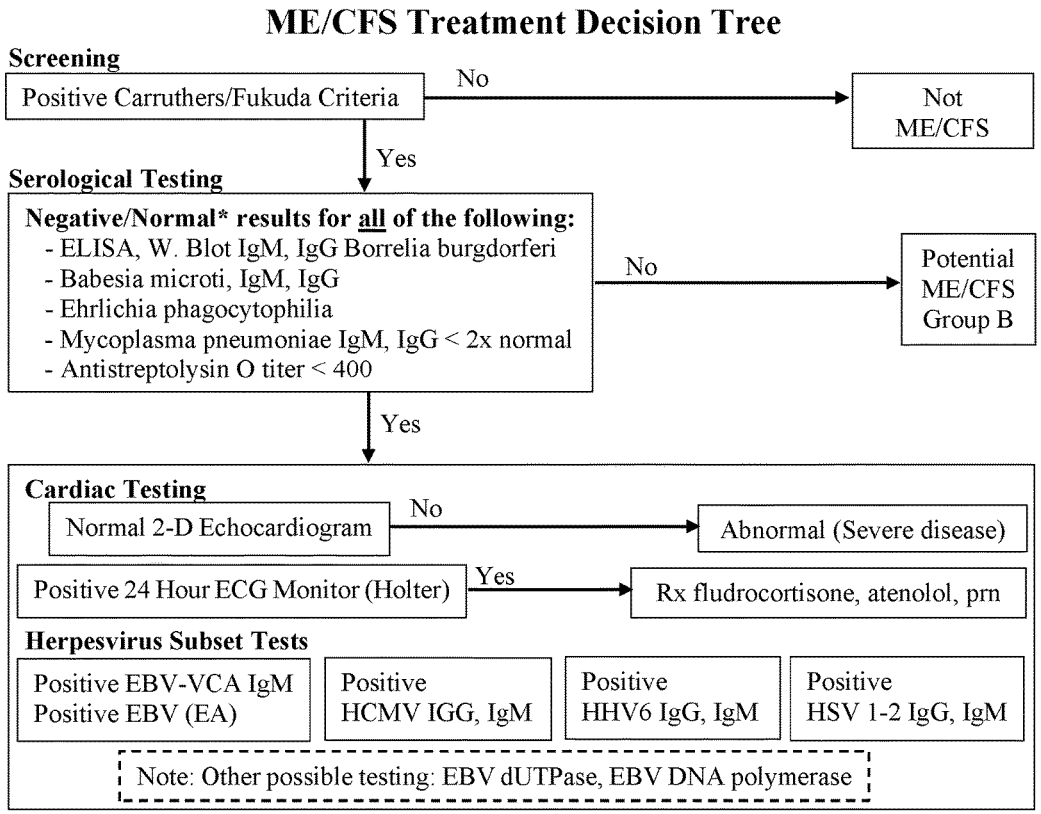

Treatment – (Duration: 1 Year)

| EBV Positive: valacyclovir/famcyclovir protocol (14.3 mg/kg po q 6hrs) Prn- cimetidine and/or probenecid | Required Safety Measures ID physician visits q 4-6 weeks. CBC, AST, ALT, Cr, UA, ECG, P.E. |
|---|---|
| CMV/HHV6 Positive: valgancyclovir protocol | |
| EBV/HHV6/HCMV Positive: valacyclovir/famciclovir/valgancyclovir protocol | |

Measure Results and Treatment
- Record EIPS®/patient/physician at each visit
- Repeat appropriate studies every 3 months
- DePaul Questionnaire @ Baseline, 6 mos, 1 yr

*LabCorp (Reference Laboratory)

METHOD OF DIAGNOSING AND TREATING EPSTEIN BARR VIRUS-BASED MYALGIC ENCEPHALOMYELITIS CHRONIC FATIGUE SYNDROME PATIENTS

TECHNICAL FIELD

The present invention relates to a method of classifying, diagnosing and treating a subset of Epstein Barr Virus, Myalgic Encephalomyelitis Chronic Fatigue Syndrome (ME/CFS) patients. In particular, the invention relates to a protocol for classifying an appropriate subset of patients through a multi-prong clinical/serological analysis, diagnosing patients with Epstein Barr virus (EBV) as the specific causal agent of chronic fatigue syndrome through the use of elevated serum antibodies to EBV encoded dUTPase and EBV encoded DNA Polymerase as molecular markers and further treating diagnosed patients with specific antiviral nucleosides which alleviate the condition.

BACKGROUND

Chronic Fatigue Syndrome (CFS), also known as myalgic encephalomyelitis (ME) and post viral fatigue syndrome, is a life altering illness affecting women to men in a ratio of 4:1. To date, evidence-based etiology or treatment has been elusive. CFS manifestations are life-altering fatigue in ordinary activities, including constellations of syncope, chest pain, muscle aches, palpitations, sore throat, low-grade fevers, and inability to exercise without a worsening of symptoms, cervical lymphadenopathy, cognitive impairment and resultant depression.

ME/CFS is not rare. The CDC estimates that there are as many as 500,000 persons in the United States who have CFS-like symptoms. However, the disorder remains debilitating, complex and mysterious in origin, natural history, understanding and treatment.

The spontaneous recovery rate for CFS patients is low, for example, 19%. Numerous treatment regimens have been proposed and include administration of various agents such as immune stimulators and steroids, as well as recommending exercise and psychiatric treatment. While they may lead to modest short-term improvement, such treatments have proven generally ineffective in the long run. As the underlying causes and distinctions among types of CFS patients have not previously been known, both observational and evidence-based trials have been misdirected or inappropriately planned.

While progress has been made to segregate certain groups of CFS patients and provide them with specific antiviral agents to alleviate the condition, for other CFS patients— namely those found to have herpes virus plus co-infections—no effective treatment option has been identified to date.

Accordingly, given the distinct types of CFS patients, underlying causative agents and varying treatment approaches, there exists a need for a methodology to identify the appropriate subset of myalgic encephalomyelitis chronic fatigue syndrome patients, a serological method to diagnose this subset and confirm the causative agent involved, so that a specific treatment protocol can be implemented to alleviate the CFS symptoms in these patients and restore their ability to lead a normal or near-normal life, free from the debilitating effects of chronic fatigue.

SUMMARY

In one embodiment of the invention, a method of diagnosing an Epstein-Barr virus subset of Myalgic Encephalomyelitis-CFS patients is disclosed, including the step of Identifying Epstein-Barr virus Abortive Lytic replication in patients with Myalgic Encephalomyelitis-Chronic Fatigue Syndrome by determining the presence of EBV encoded dUTPase or EBV encoded DNA Polymerase antibodies.

In another embodiment, a method of diagnosing an Epstein-Barr virus subset of Myalgic Encephalomyelitis-Chronic Fatigue Syndrome patients is disclosed and includes the steps of: 1) Determining the presence of encoded EBV Early Antigen, Diffuse; 2) Determining the presence of EBV encoded DNA polymerase; 3) Determining the presence of EBV encoded dUTPase; and 4) Diagnosing a patient with Epstein-Barr Abortive Lytic Replication when EBV Early Antigen, Diffuse is found in conjunction with the presence of EBV encoded DNA polymerase or EBV encoded dUTPase.

In an additional embodiment, a method of diagnosing the causation agent for a Myalgic Encephalomyelitis-Chronic Fatigue Syndrome patient is disclosed and includes the step of: Determining the absence of Epstein-Barr virus Abortive Lytic replication, through the following sub-steps: 1) Determining the absence of EBV VCA IgM; 2) Determining the absence of EBV encoded DNA polymerase; and 3) Determining the absence of EBV encoded dUTPase through assays for serum antibodies to the early EBV non-structural proteins of the EBV tegument.

In yet another embodiment, a method of diagnosing and treating an Epstein-Barr virus subset of patients with Myalgic Encephalomyelitis-Chronic Fatigue Syndrome is disclosed and includes the steps of: 1) Identifying Epstein-Barr virus Abortive Lytic replication by using EBV-encoded dUTPase and EBV-encoded DNA Polymerase as molecular markers; and 2) Treating the subset of patients with the administration of a therapeutically effective amount of at least one antiviral agent.

BRIEF DESCRIPTION OF THE DRAWINGS

FIG. 1 is a flow chart depicting the steps associated with diagnosing a patient with ME/CFS.

DETAILED DESCRIPTION

Reference will now be made in detail to embodiments and methods of the present invention which constitute the best modes of practicing the invention presently known to the inventors. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary, percent (%), "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a", "an", and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application in their entirety to more fully describe the state of the art to which this invention pertains.

The term Chronic Fatigue Syndrome (CFS) and Myalgic Encephalomyelitis Chronic Fatigue Syndrome (ME/CFS) are used synonymously herein. As used herein, CFS is defined to be a disorder caused by infection with a CFS-causing agent. "CFS-causing agent" includes CFS-inducing herpes viruses, for example, HCMV, EBV, and/or HHV6. Based on the CFS-causing agent-2 distinct patient classifications have been created. We name this group A. EB, CMV and HHV6. For group A patients the CFS-causing agent is a CFS-inducing herpes virus such as EBV, HCMV and HHV6. For group B patients, with specific co-infections, the encoded proteins may circulate by the blood stream and peripheral area, causing end-organ injury (e.g. heart, muscle, brain, liver, etc.)

The term "diagnosing: encompasses, for example, characterizing a CFS patient as belonging to a particular predefined subset of CFS causal groupings;

The term "treatment" refers to the prevention, partial alleviation or cure of the condition or disorder, or at least one symptom of the condition or disorder.

The term "effective' or "therapeutically effective" means sufficient to cause at least one of a patient's symptoms to decrease in frequency and/or intensity. To this end, one measure for effectiveness is the Energy Index point score (EIPS), which monitors the course of recovery of CFS patients under treatment by observing an increase in the EIPS of 1.0 or more units, and/or a decrease in serological indices of pathogens.

The term "infection" means the invasion of a host organism's body by another organism or entity, for example, a virus or bacteria. Infection by a virus may, but does not necessarily, include entry of the virus into host cells, production of gene products based on the viral nucleic acid, replication of the virus, and/or further spread of the virus within the host body, which may or may not induce an immunological response by the host organism. "Infection" may include the latent presence of virus, for example, that which is not replicating, and whose genes are not being expressed; or, more typically, "infection" may include a virus, at least some of whose genes are being transcribed into mRNA, which may be translated into protein gene products.

"Infection" includes abortive infection and/or replication. As used herein, "abortive" refers to infections characterized by incomplete viral replications, for example, with non-assembly into a complete virion. Abortive infection can include, for example, expression of the virus genome to produce early (IE), middle (E) or late (L) gene products including, for example, EBV encoded dUTPase and EBV encoded DNA polymerase. In such an example of abortive infection, the gene products are not assembled into a complete virus. Abortive infection may include, primarily or exclusively, early only, early and middle, or early, middle and late gene products. Abortive herpes virus replication is a proposed pathogenic mechanism of CFS that can be used to diagnose the disease, and to identify patients who are good candidates for antiviral therapy.

The term "primary abortive replication" includes, for example, first episode infection with EBV, HCMV and HHV6. The term "primary abortive replication" and "primary infection" are substantially equivalent terms.

The term "co-infection" includes infection with, for example, *Borrelia burgdorferi, Streptococcus pyogenes, Ehrlichia chaffeensis, Babesia microti* and *Mycoplasma pneumoniae*.

"Secondary nonviral infectious agent" includes, for example, *Borrelia burgdorferi, Streptococcus pyogenes, Ehrlichia chaffeensis, Babesia microti* and *Mycoplasma pneumoniae*. *Streptococcus pyogenes* infection may manifest itself as Adult Rheumatic Fever. As used herein "secondary infectious agent" and "secondary nonviral infectious agent" are substantially equivalent terms.

As used herein, "antiviral agent" includes, for example, valacyclovir, valganciclovir, maribavir, famciclovir and foscarnet. However, any antiviral agent that is effective against a CFS-inducing infection can be used according to the methods disclosed herein.

The amount of antiviral agent required to constitute a therapeutically effective amount will vary based on a number of factors, including the severity of the chronic fatigue syndrome; the identity, age, body weight, general health, gender, diet and chemical make-up of the patient; the type and degree of the cellular response to be achieved; the specific agents or composition employed, and its activity; the time of administration, route of administration, range of excretion of the agent; the duration of the treatment; drugs used in combination or coincidental with the specific agent; and like factors well-known in the medical arts. It must also take into consideration the therapeutic window, that is, the need to adjust and minimize toxic side-effects. For example, it is well within the skill of the art to start doses of the agents at levels lower than those required to achieve the desired therapeutic effect and to gradually increase the dosages until the desired effect is achieved.

Myalgia Encephalomyelitis Chronic Fatigue Syndrome (ME/CFS)

CFS was recognized as a public health problem because of recurrent signs and symptoms of this previously unknown life-altering illness. Cardiac, immune dysfunction, cerebral abnormalities have been identified. The average death age of 144 CFS registered by the National CFIDS Foundation was 39.3 years, and 20.1% died of suicide, and 20.1% of heart failure.

CFS is generally defined as a disorder of uncertain cause that is characterized by persistent, profound fatigue, usually accompanied by impairment and short-term memory or concentration, sore throat, tender lymph nodes, muscle or joint pain, and headache unrelated to any preexisting medical condition, that typically has an onset at between the ages of 30-50 of age. *Medline Plus Medical Dictionary*. CFS is often characterized by abortive replication and an inability on the part of the patient to inactivate the CFS-causing agent by inducing, for instance, inactive herpes virus latency. CFS patients can respond to antiviral therapy, as measured by, for example, a reduction in nucleic acid gene products of one or more CFS-causing agents.

Clinical tests have shown cardiac, immunologic, radiographic and genetic abnormalities in CFS patients. It was hypothesized that CFS was caused by Epstein-Barr virus (EBV), cytomegalovirus (HCMV), and human herpes virus 6 (HHV6) in single or multiple virus infection. This paradigm affirms that the herpes viruses, despite maximum efforts from these immuno-competent affected patients, continue an incomplete abortive replication of middle-gene products, usually without achieving complete virus synthesis. Per this hypothesis, CFS patients are believed to continue EBV, HCMV and HHV6 herpes virus replication, and do not achieve the viral latency necessary for recovery. As such, it was proposed that early and middle herpes virus (EBV, HCMV and HHV6) gene products to about the fiftieth gene of these complex viruses, containing over 200 open-reading frames, are synthesized without achieving complete virus formation. This hypothesis was tested with the nucleosides valacyclovir for a suspected EBV CFS subset and valganciclovir for suspected HCMV or HHV6 CFS subsets. As set forth in the International Application under Publication No. WO 2009/054957, by Dr. A. Martin Lerner, incorporated by reference herein in its entirety, specific methodologies have been disclosed to successfully classify and treat patients with EBV, HCMV and HHV6 in single or multiple infection without co-infection, through the administration of specific antiviral agents or specified treatment periods, as assessed by the validated severity of an illness metric, the Energy Index Point Score (EIPS). Further information pertaining to Dr. Lerner's work in diagnosing and treating CFS through the use of antiviral agents can be found in U.S. Pat. Nos. 5,872,123, 6,258,818, 6,399,622, 6,537,997 and 6,894, 056, which are herein incorporated by reference in their entirety.

As depicted in Table 1, the Energy Index (EI) point score (Copyright, Lerner A M and Deeter R G, 1999), is a simple and reliable metric that can be used to easily evaluate the functional capacity of the CFS patient at each patient-physician visit. The EI is measured on a scale of 1-10. Validation of the EI was done using two methods: 1.) 20 CFS patients and 22 healthy adults, matched for sex, age, place, and time; EI, CFS=3.6; EI, healthy adults=9.9, p=<0.0001; and 2.) 55 CFS patients evaluated at the same time by the EI and fatigue severity score, correlation 0.67, p=0.0066. Improvement to disappearance of CFS symptoms correlates with an increasing EI.

TABLE 1

Energy Index Point Score Metric

| Grade | Energy Expenditure (Kcal per day**) | Activity |
|---|---|---|
| 0 | 1715 | Bed-ridden, up to bathroom only |
| 1 | 1750 | Out of bed 30-60 minutes a day (sitting in chair is out of bed) |
| 2 | 1785 | Out of bed, sitting standing, walking 1-2 hours per day |
| 3 | 1855 | Out of bed, sitting standing, walking 2-4 hours per day |
| 4 | 1925 | Out of bed, sitting standing, walking 4-6 hours per day |
| 5 | 1995 | Preform with difficulty sedentary job 40 hours a week, daily naps |
| Recovery | | |
| 6 | 2083 | Daily naps in bed, may maintain a 40 hour sedentary work week plus light, limited housekeeping and/or social activities |
| 7 | 2205 | No naps in bed. Up 7:00 a.m. to 9:00 p.m. Able to work a sedentary job plus light housekeeping |
| 8 | 2240 | Full sedentary workweek, no npas, some social activities plus light exercise |
| 9 | 2450 | Same as 8 above plus exercise approximately ½ to ⅔ normal without excessive fatigue, awakens next morning refreshed |
| 10 | >2500 | Normal |

*The CFS Energy Index point score can also be determined by questionnaire (US copyright, 1999 Lerner A. M., Deeter, R. J) reproduced with permission
**Kcal per day is calculated for a 70 kg CFS patient The validated energy index point score generally can be calculated for each CFS patient every 3 months at physician visits. A CFS patient has an EI≤5. A CFS patient with an EI of 0 is bedridden; a CFS diagnosis is no longer present at an EI>5. The EI effect size is 0.25, a medium effect size is 0.5. A large effect size is >0.8.

While CFS patients classified with EBV, HCMV and HHV6 in single or multiple infections without co-infection have been diagnosed and treated successfully, that is not the case to date for the group of EBV subset CFS patients with co-infections, such as tick-borne *Borrelia burgdorferi, Babesia microti, Anaplasma phagocytophila* and/or adult rheumatic fever. For this group of patients, their ability to lead fulfilling and productive lives has to-date remained significantly compromised. This invention addresses this long standing, but unmet need.

Epstein-Barr Virus

Epstein-Barr virus (EBV), a gamma herpes virus, is one of the causative agents of the Chronic Fatigue Syndrome. EBV, like other herpes viruses, encodes for several enzymes that are involved in viral DNA replication; all are part of the early antigen (EA) complex. Several EBV-associated enzymes have been described to date, such as thymidine kinase (TK), Deoxyribonucleotide polymerase (DNA polymerase), deoxyribonuclease (DNASE), deoxyuridine Triphosphate Nucleotidohydrolase (dUTPase), and ribonucleotide reductase, as well as uracil-DNA glycosylase. Historically, while these antibodies to EBV-encoded enzymes were observed in patients with different EBV-associated diseases, the reason for these antibody patterns and the role these proteins might play in the pathophysiology of disease, separate from their role in virus replication has been unknown. Some hypotheses were described in an article entitled "Stress-associated changes in the steady-state expression of latent Epstein-Barr virus: Implications for chronic fatigue syndrome and cancer" in *Brain, Behavior and Immunity* 10 (2005) 90-103, incorporated by reference herein.

Creation of a ME/CFS Diagnostic Panel & the Identification of Molecular Markers

A ME/CFS diagnostic panel was created utilizing initial Fukuda/Carruthers criteria and a systematic review of 142 ME/CFS patients. Two groups of ME/CFS patients were found. Group A patients had elevated serum IgG antibody titers to the herpes viruses Epstein-Barr virus (EBV), cytomegalovirus (HCMV) and Human Herpes virus 6 (HHV6) in single or multiple virus infection, but no other co-infections. Group B patients had similar elevated herpes virus antibody titers, plus serologic evidence of co-infections, tick-borne ("Borrelia burgdorferi", "Anaplasma phagocytophilia", "Babesia microti"); "Mycoplasma pneumoniae"; or adult rheumatoid fever. One hundred and six group A ME/CFS patients were followed from 2001-2007, and treated with subset directed valacyclovir EBV subset or valganciclovir (HCMV, HHV6 subsets). The data included over 7000 patient visits and 35,000 data entries. Seventy-nine (74.5%) of the group A patients recovered to resume normal life ($p<0.0001$)—the results are unprecedented.

Notwithstanding the advances made, until now an evidence-based simple test for the diagnosis of ME/CFS has remained elusive. Dr. Glaser in conjunction with Dr. Williams and Dr. Lerner, independently suggested that ME/CFS is abortive lytic herpes virus replication without DNAemia, antigenemia or IgM antibody to herpes virus structural antigens. Drs Glaser and Williams found that the early EBV protein dUTPase produced both illness behavior in a murine model, and immunologic abnormalities in peripheral blood mononuclear cells in vitro. Similar immunologic disarray with quantitative changes of intracellular perforins and granzymes were found in ME/CFS patients. Since valacyclovir and valganciclovir do not inhibit early herpes virus proteins, it was suggested that new herpes virus host cell recruitment had been interrupted in the ME/CFS patients who had recovered their health. Valacyclovir after gastrointestinal absorption has a 200× greater affinity for EBV thymidine kinase than for the host cellular enzyme. (1) Valganciclovir inhibits HCMV and HV6 DNA polymerases. As such, it was believed that herpes virus early proteins may be critical in the etiology of ME/CFS.

In this regard in patients with HCMV subset ME/CFS, a unique presence of IgM HCMV early proteins p52 (UL44) and CM2 (UL 44-UL 57) was detected in 61 HCMV subset patients, but these serum antibodies were not found in a comparison group of well patients. It was thus reported that elevated serum antibody titers to EBV (EA,D) in 86 of the 106 (81%) ME/CFS patients with group A ME/CFS were found.

EBV early gene proteins dUTPase and DNA polymerase are enzymes involved in EBV lytic DNA replication. A repetitive presence of positive serum antibodies to EBV encoded gene products dUTPase and DNA polymerase has been found in 6 EBV subset ME/CFS patients. Over a period of 13-16 consecutive months from 2003-2007, serum assays from these 6 EBV subset ME/CFS patients tested positive to EBV dUTPase in 25/50 assays (50%) and to EBV DNA polymerase 40/52 assays (76.9%). Comparison group assays for EBV dUTPase and EBV DNA polymerase from 20 control age-sex matched persons were negative. The presence of the EBV proteins dUTPase and DNA polymerase in the blood of ME/CFS patients indicate abortive lytic replication. Accordingly, the presence of serum antibodies to EBV, dUTPase and EBV DNA polymerase are believed to be diagnostic molecular markers for the EBV subset of ME/CFS patients.

Testing Methods
ME/CFS Patients

6 ME/CFS patients were identified as Group A EBV subset (five patients), and one patient (group B) had co-infection with Borrelia burgdorferi. The single ME/CFS group B patient had a positive Borrelia burgdorferi western blot IgM test. A ME/CFS treatment decision tree that developed from the systematic review of the 142 ME/CFS patients is provided as FIG. 1.

Comparison Group

Blood samples were taken from unknown persons at a commercial laboratory. The age and sex of the comparison group were selected to be similar to ME/CFS patients.

EBV, VCA, IgM, VCA p18 peptide is a defined VCA-specific marker protein utilized in the ETI-EBV-M reverse assay (DiaSorin, Inc., Stillwater, Minn., USA). It consists of 56 amino acids of the BFRF encoded VCA and contains immune-dominant epitopes. This ETI-EBV-M reverse kit utilizes the enzyme-linked immunosorbent assay (ELISA) based on the antibody capture technique. The absorbance of the solution measured at 450 nm is related to the concentration of IgM to EBV VCA present in the reaction solution.

EBV-IgG Early Antigen (diffuse), EA(D). The ETI-EA-G kit (DiaSorin) for quantitative detection of IgG antibodies to EBV Early Antigen Diffuse (EBV-EA (D) was used. Diluted serum was incubated with recombinant EA(D) peptide bound to the solid surface of a micro titer well. The ETI-EA-G assay uses an EA(D) 47 KD recombinant polypeptide. The absorbance of the solution, measured at 450 nm is proportional to the concentration of IgG antibodies to EBV EA(D) present in the reaction solution.

HCMV ELISA testing for CMV IgG and CMV IgM was performed using ELISA kits from DiaSorin. The HCMV IgG kit contains purified HCMV strain AD-169 antigen-coated wells. The HCMV IgM ELISA is a microcapture assay with wells coated with anti-human IgM antibody to the same strain AD-169. Sera were diluted 1:10 and incubated for one hour at 37° C. The wells were washed three times in washing buffer and bound HRP label was detected with 3,3' 5.5 tetramethyl benzidine as substrate for 30 minutes in the dark, after which the color reaction was stopped by the addition of stop solution as recommended by the manufacturer's manual. The absorbance was measured at 450/650 nm using Biotech reader (Biotech Clinical Laboratories, Inc., Farmington Mich., USA).

Neutralization assays (DNA polymerase, DNase, and dUTPase) were performed as previously described. Briefly, 5 µl of human serum were mixed with 5 µl of either purified EBV-encoded dUTPase (3-5 units of enzyme) or an extract from TPA/sodium butyrate induced Raji cells (for EBV-encoded DNA polymerase) for 30 min at room temperature prior to assaying for enzymatic activity. EBV-encoded DNA polymerase and dUTPase activity were determined as described previously. Raji cells were induced by treatment with TPA and sodium butyrate for 48 hrs. Cells (106-8) were harvested, re-suspended in 1 ml of extraction buffer (50 mm Tris-HCl, pH 8.0 2 mM ATP, 0.2 M KCl, 3 mM dithiothreitol, 2 mM MgCl2 0.2 mM phenylmethylsulfonylfluoride and 10% (v/v) glycerol, lysed by sonication and centrifuged at 14,000×g for 5 min. The resulting supernatant was employed for the EBV-encoded DNA polymerase assay. Purified EBV-encoded dUTPase was also obtained as previously described.

For positive controls, assays were performed in the absence of human sera that lacked detectable antibodies to the EBV encoded dUTPase and DNA polymerase and negative controls were performed in the absence of the enzyme preparation. Units neutralized were obtained as follows:

(Ucontrol-Userum). Serum with neutralizing units greater than or equal to two standard deviations from the control are considered "positive" for dUTPase or DNA polymerase neutralizing antibodies.

The following tests were performed by Lab Corps (Dublin, Ohio) on the 6 ME/CFS patients (Groups, A 5 patients, Group B, 1 patient) 163600 Lyme, Western Blot and ELISA, serum—IgG and IgM. Method. Antigen—whole-cell proteins were extracted from *B. burgdorferi* strain B31, resolved by polyacrylamide gel electrophoresis into individual antigen bands and then transferred to nitrocellulose strips for blotting.

*Babesia microti* Antibody Panel—IgG and IgM. Method-IFA. Antigen—the substrate for the IFA was guinea pig or hamster erythrocytes infected with *Babesia microti* organisms and then fixed onto microscope slides. Upon interaction with human sera containing anti-*Babesia* antibodies and the appropriate conjugate, infected cells fluoresce.

138315 *Ehrlichia* Ab panel "(Granulocytic and Monocytic/Anaplasma phagocytophilia)"—IgG and IgM. Method: IFA. Antigen: is either inactivated HGE or HME 163758 *Mycoplasma pneumoniae* Antibodies—IgG and IgM. Method: EIA. Antigen: *Mycoplasma pneumoniae* FH antigen 006031 Antistreptolysin 0 Ab. Method: Latex immunoturbidimetry. Human Antistreptolysin 0 antibodies agglutinate with latex particles coated with streptolysin 0 antigens. The precipitate is determined turbidimetrically at 552 nm.

Results
ME/CFS Patients (Table 2)

Demographics. ME/CFS patients (Table 2) the six ME/CFS patients (5 women) were selected from 142 ME/CFS of the 2001-2007 systematic review. They were 37-59 years old. Serum samples were taken at intervals Mar. 5, 2002-Nov. 14, 2003. There were 7 to 10 sera from each patient. Five of the 6 ME/CFS patients were Group A (no co-infections), and one patient had co-infection with *Borrelia burgdorferi* (patient no. 2). Five of the 6 patients were HCMV IgG serum antibody negative. Initial EIPS values were 3.5-5.0, meaning that patients could be out of bed only 3 to 4 hours a day, and required daily naps in bed to complete each day. One ME/CFS patient was able to struggle to complete a sedentary working day (Table 2, patient no. 6). The solitary man of these 6 "ME/CFS" patients did not meet criteria for ME/CFS at baseline (EIPS, 6). He struggled at baseline to maintain his sedentary working day, required a daytime nap, and could no longer do any exercise without marked syncope and worsening fatigue. One year later the final EIPS values were 7-8, for the 5 group A ME/CFS patients, meaning that patients could now live normal lives. The single group B ME/CFS patient's final EIPS value increased from a baseline of 3.5 to 5, but this woman still met international criteria diagnosis of ME/CFS. The EIPS is a validated (FSS-9 item scale with high degree of internal consistency measured by Cronbach's alpha) is a Functional Activity Appraisal: energy Index Score Healthcare worker Appraisal.

EBV Encoded Gene Products EBV, VCA IgM Forty-nine VCA IgM assays were done. All were negative.

EBV, EA (D) Forty-nine EA (D) assays were done. All were positive except two sera from ME/CFS patient number 6 whose baseline EIPS value was 6. Mean patient EBV (EA) titers were: 54 (patient one); 123 (patient two); 63 (patient three); 128 (patient four); 49 (patient five); and 27 (patient six), negative<20. The mean EA (D) titer for these 6 patients was 74.

EBV dUTPase Three of 9 (33.3%), ME/CFS (patient one); 5 of 7 (71.4%) ME/CFS (patient two); 3 of 9 (33%) ME/CFS (patient three); 8 of 10 (80%) ME/CFS (patient four); 3 of 8 (37.5%) ME/CFS (patient five); 3 of 7 (43%) ME/CFS (patient six) were positive assays for elevated serum antibody titers to EBV dUTPase. Twenty-five of the 50 (50%) assays were positive.

EBV DNA polymerase. Eight of 10 (80%) of ME/CFS (patient one); 4 of 7 (57.1%) ME/CFS (patient two); 7 of 10 (70%) ME/CFS (patient three); 9 of 10 (90%) ME/CFS (patient four); 7 of 8 (88%) ME/CFS (patient five); and 3 of 5 (71.4%) (patient six) were positive serum assays for elevated antibody titers to EBV DNA polymerase. Forty of the 52 (76.9%) ME/CFS assays from ME/CFS patients were positive.

Comparison Group Patients (Table 3)
Demographics

The mean age of the comparison group was 48.7 years (36-59). Fifteen of 19 (78.9%) persons were women. EBV, VCA, IgM Twenty assays from the comparison group were done. All were negative.

EBV, EA (D) Twenty assays from the comparison group were done. Fourteen comparison group patients had negative EV EA (D) titers. Six comparison group patients had EBV (EA) titers. The mean EA (D) of the comparison group was 22.

EBV dUTPase twenty assays from the comparison group were done. All were negative.

EBV DNA polymerase twenty assays from the comparison group were done. All were negative.

Analysis of Tables 2 and 3

These data demonstrate the presence of elevated serum antibodies to encoded EBV non-structural proteins DNA polymerase (EBV poly) and dUTPase (EBV dUTP) in blood from six EBV subset ME/CFS patients. These antibodies in the blood samples of ME/CFS patients accompany their likely source, a "primary" plasma cell apoptosis. EBV poly and dUTP-emias are being monitored in the ME/CFS patients. It is believed that EBV lytic virus had likely originated in pharyngeal epithelial cells to then infect adjacent memory B cells where the EBV genome was latent. As memory B cells differentiate to plasma cells, they are believed to be the probable site of the current early encoded EBV proteinemia abortive lytic replication. While the early EBV protein BZLF1 (Zta, EB1) initiates the EBV viral lytic cycle, only 15% of B cells expressing BZLF1 achieve a full lytic cycle to primary infection (infectious mononucleosis)—completing the virion. The majority replication is abortive lytic in type. It is believed that BZLF1 and dUTPase in vitro induce a cellular dysregulation, with TNF and Fasligand. It is further believed that the encoded circulating proteins BZLF1, dUTPase, DNA polymerase and, likely, other EBV encoded tegument early proteins may enter host cells of affected ME/CFS patient's organs, namely heart, striated muscle, and the brain to initiate a secondary expansive apoptosis along with IL-6, I-10, TGF-B, tyrosine Kinase, TKT matrix metalloproteinase and C-Fos. This secondary ME/CFS apoptosis is believed to be the pathologic mechanism of ME/CFS and does not require EBV DNA, and further may de-mystify and explain the difficulty in associating EBV replication and ME/CFS.

The proteins EBV dUTPase and EBV DNA polymerase separate the EBV subset ME/CFS patients from 20 comparison group patients, and, thus, offer a possible molecular marker for the diagnosis of EBV subset ME/CFS patients. Assays for EBV, VCA IgM; EBV, EA(D); EBV dUTPase and EBV DNA polymerase along with Fukada/Carruthers ME/CFS criteria and the confirming diagnostic panel described define the EBV subset of ME/CFS patients. (Table 2) Five of the six ME/CFS patients at baseline met international criteria for ME/CFS. The single male was chronically ill, could not work regularly or exercise.

Forty-nine EBV VCA IgM serum assays taken serially over 13-16 months were negative. Comparison group assays for EBV VCA IgM, EBV dUTPase and EBV DNA polymerase were negative. However, 47/49 (95.9%) EBV EA (D) assays from ME/CFS patients were positive. Twenty-five of 50 (50%) dUTPase antibody serum assays were positive and 40/52 (76.9%) DNA polymerase serum antibody assays were positive from the ME/CFS patients. The results describe abortive lytic EBV replication of early viral proteins EA(D) dUTPase, and DNA polymerase which have been released from infected cells into the blood. These aberrant virus tegument-belonging, intracellular belonging proteins and, perhaps, other early EBV proteins may traverse cellular membranes of multiple host systems stimulating the immune dysregulation and the symptoms of ME/CFS. Serum antibodies of EBV dUTPase and EBV DNA polymerase in blood samples of ME/CFS patients, who have been treated or not treated with valacyclovir are present for over 400 days.

EBV dUTPase (BLLF3) is a part of this EBV early antigen complex. EBV DNA polymerase (BALF5) is an early protein heralding EB lytic replication. EBV DUTPase catalyzes the hydrolysis of dUTP to dUMP, preventing incorporation of uracil into replicating DNA. EBV DNA polymerase is necessary for EBV lytic replication. EBV dUTPase and EBV Zta (BZLF1, 2EBRA, EB1) induce widespread immune dysregulation. Accordingly, abortive lytic EBV replication may be responsible for the cardiomyopathy/encephalopathy of ME/CFS.

In addition to the EBV subset of ME/CFS patients, space flights also lead to reduced T-cell function, altered leukocyte and lymphocyte subsets, decreased delayed type hypersensitivity and altered cytokine production. Elevated levels of glucocorticoids are present during and after space flights. B-lymphocytes from 6 astronauts who flew ~180 day space flights showed expanded expression of EBV latent, immediate early and early gene transcripts and EBV late replicative transcription upon return to earth. Under such conditions, EBV undergoes abortive lytic replication like the EBV subset ME/CFS patients.

TABLE 2

EBV ABORTIVE LYTIC REPLICATION IN SIX EBV SUBSET ME/CFS PATIENTS TREATED WITH VALACYCLOVIR FOR ≥12 MONTHS

| Patient No. | Age | Sex | Sera | Date | EA(D) (<20) | VCA, IGM (<20) | dUTPase | DNA Polymerase |
|---|---|---|---|---|---|---|---|---|
| 1 | 37 | F | 1 | Mar. 12, 2002 | 53 | Negative | Positive | Negative |
| Group A | | | 2 | Apr. 23, 2002 | Not done | Not done | Negative | Positive |
| ME/CFS | | | 3 | Jun. 27, 2002 | 50 | Negative | Positive | Positive |
| Co- | | | 4 | Sep. 28, 2002 | 36 | Negative | Negative | Positive |
| infection | | | 5 | Oct. 22, 2002 | 74 | Negative | Not done | Positive |
| None | | | 6 | Nov. 21, 2002 | 115 | Negative | Negative | Positive |
| EIPS 5 | | | 7 | Jan. 9, 2003 | 70 | Negative | Negative | Negative |
| baseline | | | 8 | Mar. 6, 2003 | 51 | Negative | Negative | Positive |
| EIPS 8 | | | 9 | May 1, 2003 | 45 | Negative | Positive | Positive |
| final | | | 10 | Jun. 10, 2003 | 42 | Negative | Negative | Positive |
| Totals | | | 10 sera | 14 months | 54 (mean) | 0/9 (0%) | 3/9 (33%) | 8/10 (80%) |
| 2 | 43 | F | 1 | Mar. 22, 2002 | 116 | Negative | Positive | Positive |
| Group B | | | 2 | May 17, 2002 | 125 | Negative | Positive | Positive |
| ME/CFS | | | 3 | Sep. 26, 2002 | 120 | Negative | Positive | Positive |
| Co- | | | 4 | Oct. 24, 2002 | 123 | Negative | Positive | Positive |
| Infection | | | 5 | Nov. 21, 2002 | 150 | Negative | Negative | Negative |
| Lyme | | | 6 | Mar. 12, 2003 | 104 | Negative | Negative | Negative |
| Disease | | | 7 | May 9, 2003 | 121 | Negative | Positive | Negative |
| EIPS 3.5 | | | | | | | | |
| baseline | | | | | | | | |
| EIPS 5 | | | | | | | | |
| final | | | | | | | | |
| Totals | | | 7 sera | 13 months | 123 (mean) | 0/7 (0%) | 5/7 (71.4%) | 4/7 (57.1%) |

| Patient No. | Age | Sex | Sera | Date | EA(D) | VCA, IGM | dUTPase | DNA Polymerase |
|---|---|---|---|---|---|---|---|---|
| 3 | 46 | F | 1 | Mar. 12, 2002 | 63 | Negative | Positive | Negative |
| Group A | | | 2 | Apr. 19, 2002 | 70 | Not done | Negative | Positive |
| ME/CFS | | | 3 | Jun. 28, 2002 | 45 | Negative | Positive | Positive |
| Co- | | | 4 | Aug. 5, 2002 | 75 | Negative | Negative | Positive |
| infection | | | 5 | Sep. 17, 2002 | 54 | Negative | Not done | Positive |
| None. | | | 6 | Oct. 31, 2002 | 100 | Negative | Negative | Positive |
| EIPS 5 | | | 7 | Nov. 21, 2002 | Not done | Negative | Negative | Negative |
| baseline | | | 8 | Feb. 6, 2003 | 47 | Negative | Negative | Positive |
| EIPS 8 | | | 9 | Mar. 20, 2003 | 67 | Negative | Positive | Positive |
| final | | | 10 | Jun. 20, 2003 | 49 | Negative | Negative | Positive |
| Co- | | | | | | | | |
| morbidity | | | | | | | | |
| Cancer of | | | | | | | | |
| breast | | | | | | | | |
| Totals | | | 10 sera | 14 months | 63 (mean) | 0/9 (100%) | 3/9 (33%) | 7/10 (70%) |
| 4 | 59 | F | 1 | Jun. 19, 2002 | 150 | Negative | Positive | Positive |
| Group A | | | 2 | Aug. 6, 2002 | 122 | Negative | Positive | Negative |

TABLE 2-continued

EBV ABORTIVE LYTIC REPLICATION IN SIX EBV SUBSET ME/CFS
PATIENTS TREATED WITH VALACYCLOVIR FOR ≥12 MONTHS

| | | | | | | | | |
|---|---|---|---|---|---|---|---|---|
| ME/CFS | | | 3 | Oct. 8, 2002 | 129 | Negative | Positive | Positive |
| Co-infection | | | 4 | Nov. 7, 2002 | 184 | Negative | Negative | Positive |
| None | | | 5 | Dec. 3, 2002 | 149 | Negative | Positive | Positive |
| EIPS 4 | | | 6 | Feb. 4, 2003 | 131 | Negative | Positive | Positive |
| baseline | | | 7 | Mar. 18, 2003 | 134 | Negative | Positive | Positive |
| EIPS 7 | | | 8 | May 15, 2003 | 86 | Negative | Positive | Positive |
| final | | | 9 | Jul. 10, 2003 | 89 | Negative | Positive | Positive |
| Co-morbidity | | | 10 | Nov. 14, 2003 | 105 | Negative | Negative | Positive |
| Cancer of breast | | | | | | | | |
| Totals | | | 10 sera | 16 months | 128 (mean) | 0/10 (0%) | 8/10 (80%) | 9/10 (90%) |
| 5 | 59 | F | 1 | Apr. 4, 2002 | 38 | Negative | Positive | Negative |
| Group A | | | 2 | May 16, 2002 | 58 | Negative | Negative | Positive |
| ME/CFS | | | 3 | Jun. 27, 2002 | Not done | Not done | Negative | Positive |
| EBV/HCM | | | 4 | Aug. 18, 2002 | 45 | Negative | Negative | Positive |
| V subset | | | 5 | Oct. 29, 2002 | 43 | Negative | Negative | Positive |
| EIPS, N/A | | | 6 | Dec. 12, 2002 | 54 | Negative | Negative | Positive |
| Diabetes | | | 7 | Apr. 10, 2003 | 75 | Negative | Positive | Positive |
| Mellitus Type 2 | | | 8 | May 30, 2003 | 27 | Negative | Positive | Positive |
| Congestive heart Failure | | | | | | | | |
| Totals | | | 8 sera | 13 months | 49 (mean) | 0/7 (0%) | 3/8 (37.5%) | 7/8 (88%) |
| 6 | 59 | M | 1 | Mar. 5, 2002 | Neg. | Negative | Positive | Negative |
| Group A | | | 2 | Apr. 6, 2002 | 25 | Negative | Negative | Positive |
| ME/CFS | | | 3 | Sep. 11, 2002 | 32 | Negative | Positive | Negative |
| Co-infections - | | | 4 | Dec. 19, 2002 | 23 | Negative | Positive | Positive |
| None | | | 5 | Mar. 14, 2003 | Neg. | Negative | Negative | Positive |
| EIPS 6 | | | 6 | May 5, 2003 | 28 | Negative | Negative | Positive |
| baseline | | | 7 | Jun. 17, 2003 | Neg. | Negative | Negative | Positive |
| EIPS 7 final | | | | | | | | |
| Totals | | | 7 sera | 14 months | 27 (mean) | 0/7 (0%) | 3/7 (43%) | 5/7 (71.4%) |

TABLE 3

EBV Abortive Lytic Replication in Twenty Comparison Group Patients

| Patient No. | Age | Sex | Sera | Date | EA(D) (<20) | VCA, IGM (<20) | dUTPase | DNA Polymerase |
|---|---|---|---|---|---|---|---|---|
| 1 | 38 | F | 1 | Jun. 28, 2011 | 68 | Negative | Negative | Negative |
| 2 | 43 | F | 2 | Jun. 28, 2011 | 8 | Negative | Negative | Negative |
| 3 | 45 | F | 3 | Jun. 28, 2011 | 75 | Negative | Negative | Negative |
| 4 | 59 | F | 4 | Jun. 28, 2011 | 9 | Negative | Negative | Negative |
| 5 | 59 | F | 5 | Jun. 28, 2011 | 24 | Negative | Negative | Negative |
| 6 | 59 | M | 6 | Jun. 28, 2011 | 13 | Negative | Negative | Negative |
| 7 | 37 | F | 7 | Jun. 28, 2011 | 54 | Negative | Negative | Negative |
| 8 | 44 | F | 8 | Jun. 28, 2011 | 12 | Negative | Negative | Negative |
| 9 | 46 | F | 9 | Jun. 28, 2011 | 12 | Negative | Negative | Negative |
| 10 | 59 | F | 10 | Jun. 28, 2011 | 9 | Negative | Negative | Negative |
| 11 | 59 | F | 11 | Jun. 28, 2011 | 6 | Negative | Negative | Negative |
| 12 | 60 | M | 12 | Jun. 28, 2011 | 7 | Negative | Negative | Negative |
| 13 | 59 | M | 13 | Jun. 28, 2011 | 9 | Negative | Negative | Negative |
| 14 | 47 | M | 14 | Jun. 28, 2011 | Not done | Negative | Negative | Negative |
| 15 | | | 15 | Jun. 28, 2011 | 10 | Negative | Negative | Negative |
| 16 | 43 | F | 16 | Jun. 28, 2011 | 9 | Negative | Negative | Negative |
| 17 | 44 | F | 17 | Jun. 28, 2011 | 19 | Negative | Negative | Negative |
| 18 | 36 | F | 18 | Jun. 28, 2011 | 35 | Negative | Negative | Negative |
| 19 | 38 | F | 19 | Jun. 28, 2011 | 6 | Negative | Negative | Negative |
| 20 | 50 | F | 20 | Jun. 28, 2011 | 53 | Negative | Negative | Negative |
| Comparison Group | (Mean) 48.7 yrs (36-59) | 15/19 78.9% Female | | Jun. 28, 2011 | 6/20 > 20 (30%) Positive 22 (mean) | 0/20 (0%) | 0/20 (0%) | 0/20 (0%) positive |
| ME patients | 57.0 yrs (37-59) | 5/6 83.3% Female | | Jun. 28, 2011 | 47/49 > 20 (95.9%) positive 74 (mean) | 0/49 (0%) positive | 25/50 (50%) positive | 40/52 (76.9%) positive |

In another aspect, the invention provides methods of diagnosing an EBV subset of CFS patients, comprising selecting a set of target serologic markers of a plurality of pathogens, wherein the pathogens are associated with CFS—in this case the identification of the molecular markers for EBV, DNA polymerase and dUTPase; obtaining a set of quantitative values for a reference level for each of the serologic markers in the set, wherein a level of serologic marker above the reference level indicates the presence of a pathologic level of the pathogen in the physiological fluid tested; obtaining from the patient a sample of physiological fluid in which the target serologic markers would be found if the pathogen is present in the patient; measuring the serologic levels for each of the target serologic markers in the physiologic fluid of the patient in obtaining a quantity that value for the serologic level of each target serologic marker, comparing the serologic level with the reference level for each target serologic marker; and identifying the patient as having EBV abortive lytic replication if the identified molecular markers are significantly above the reference level. As used herein, a serologic level is significantly above the reference level if the serologic level exceeds the reference level to the degree that it would indicate the presence of an infection to a person of ordinary skill in the art. "Serologic marker" encompasses any serologic evidence that indicates the presence of the pathogen in the patient's body. Such evidence can include, for example, the presence of a molecule or other entity—such as the two molecular markers identified herein for the EBV subset of CFS patient—that is generally not present in the healthy individual; increase or decrease of the level of the molecule or other entity of what is generally present in healthy individual; or any other indicator know in the arts.

During the initial primary herpes virus infection, EBV antibodies to multiple early, middle and late gene products, as well as those to complete virus particles, are produced, which may give rise to serum-specific IgM antibody titers two multiple gene products. Then, as the patient recovers all serum antibody titers to early, middle and late herpes virus nonstructural genes disappear, any only positive serum antibody titers to complete structural virions, such as serum-specific IgG remain.

In CFS, however, there is "abortive" herpes virus infection with no compete virion multiplication, and products in the periphery may induce elevated serum antibody titers.

Therefore, in EBV subset CFS there may be elevated serum antibody titers to EBV early, middle and late gene products not ordinarily present. In group A CFS in which abortive replication by two or three of the EBV, HCMV, HHV6 is present, appropriate dual or triple herpes virus elevated early, middle, late serum antibody titers to gene products may be found.

Experimental Approaches to Developing Serological Assays

To specifically diagnose ME/CFS, serological assays need to be prepared based on EBV viral products specific to the ME/CFS diagnosis. As such, in one embodiment, a combination of several gene products specific for viral replication, representing active viral replication will be used to develop multiplex immunoassays. Such immunoassays will preferably be developed on a Luminex TM 100×MA platform using microsphere immunofluorescent bead technology capable of simultaneously analyzing a single specimen for multiple analytes.

Analytical validation are preferably performed for each antigen in a singleplex assay, and then all together in a multiplex assay. Preferably, analytical sensitivity and specificity within the detection limit are performed for each antigen individually in a singleplex assay and then combined in a multiplex assay.

a) Selection of Antigens Based on EBV Viral Genes

Candidates for IgM and/or IgG should be assayed and developed. Different antigens may be used for this assay, such as: 1) For IgG serological assay, EBV-EA composed of EBV-EA-D recombinant proteins which are specific for EBV IgG will be used as an internal control to monitor the IgG response to these antigens; 2) For EBV IgM serology, two new antigens may be used for this assay: EBV encoded dUTPase and the EBV DNA encoded polymerase gene products in combination, and EBV VCA IgM or VCA p18 peptide (considered as IgM for EBV serology) will be used; and 3) EBV VCA IgM will be used as an internal control for IgM serology.

EBV encoded dUTPase and the EBV DNA encoded polymerase gene products have been shown to be specific for abortive lytic EBV replication in ME/CFS patients and thus, developing a multiplex immunoassay using this specific combination of highly defined recombinant viral proteins will offer a unique diagnostic tool for detection and differentiation of EBV infection in ME/CFS patients. In addition, this test's utility can be expanded to serological testing for infection in immuno-compromised patients including those infected with HIV.

b) Cloning of the Candidate Genes

Plasmids with clones of EBV encoded dUTPase and the EBV DNA encoded polymerase gene products are available and can be expressed using known cloning plasmid and expression systems.

c) Production and Purification of Antigens (Cloned Genes)

While antigens will generally be produced in a laboratory, EBV EA and EBV VCA IgM antigens are commercially available.

d) Luminex Technology Platform.

Luminex's xMAP technology, based upon flow cytometry, color-codes tiny beads, called microspheres, into 100 distinct sets. Each bead set can be coated with a reagent specific to a particular bioassay (antigens) allowing the capture and detection of specific analytes from a sample. In this way, xMAP technology is well suited to assay development by allowing multiplexing of up to 100 unique assays within a single sample, both rapidly and precisely.

e) Selection and Activation of Luminex Microsphere Beads

The antigens will be coupled to the Luminex microspheres by using N-hydroxysulfosuccinimide enhanced carbodiimide-mediate coupling reaction.

f) Covalent Coupling of Selected Antigens to Luminex Microspheres (Beads)

In a preferred embodiment, the selected antigens: EBV EA and EBV VCA-IgM and EBV encoded dUTPase and the EBV DNA encoded polymerase gene products/antigen will be diluted in a Phosphate Buffering Solution (PBS) to a concentration of 12 µg/ml. A total of 500 µl of the antigens/antibodies (12 µg/ml) will be added to the activated microsphere and vortex on a low setting for 10-20 seconds to re-suspend the microspheres. The antigens will be coupled to the microsphere as follows: EBV EA to microsphere #32, EBV VCA IgM to microsphere #53, EBV encoded dUTPase to microsphere #38, EBV DNA encoded polymerase to microsphere #25. Calibrators containing different concentrations of EBV EA and EBV IgM will serve as an internal control that will monitor the validity of the assay, they will be covalently attached to microspheres #1, #10, #15 and #20. These selected microspheres are different in color, which aids spectral resolution. Similarly, the listed antigens will be individually coupled to selected microspheres.

g) Multiplex Luminex Immunoassay

The Luminex Multiplex Immunoassay is designed to detect specific EBV antibodies in human sera to a variety of EBV antigens. The test procedure involves two incubation steps:

Step 1. Test sera (properly diluted) are incubated in a vessel containing a multiplexed mixture of the bead suspension. The multiplexed bead suspension contains a mixture of distinguishable sets of polystyrene microspheres. For IgG; Three of these bead sets are conjugated with the EBV-EA, EBV encoded dUTPase and the EBV DNA encoded polymerase gene products.

For IgM serology the multiplexed bead suspension contains a mixture of distinguishable sets of polystyrene microspheres; Three of these bead sets are conjugated with the EBV-VCA IgM, EBV encoded dUTPase and the EBV DNA encoded polymerase gene products. The bead mix also contains one bead set designed to detect non-specific binding and four separate bead sets are used for assay calibration. If present in patient sera, specific antibodies will bind to the immobilized antigen on one or more of the bead sets. The microspheres are then rinsed to remove non-reactive serum proteins.

Step 2. Phycoerythrin-conjugated goat anti-human IgG (Fc chain specific from Chemicon Inc) is added to the vessel and the plate is incubated. The conjugate will react with IgG antibody immobilized on the solid phase in step 1. The bead suspension is then analyzed by the Luminex 100 instrument. The bead set(s) are sorted (identified) and the amount of reporter molecule (PE conjugate) is determined for each bead set. Internal calibration bead sets are used to convert raw fluorescence into outcome (units).

h) Optimization and Validation of the Assay (Test Verification)

Analytical validation will be performed for each antigen in a singleplex assay, and then all together in a multiplex assay. Analytical sensitivity and specificity with limit of detection will be performed for each antigen individually in a singleplex assay and then all together in a multiplex assay. Different concentrations of each antigen will be used for sensitivity and specificity studies ranging from the lowest detection limit through the highest detection limit. In addition, reproducibility, repeatability and precision studies will be performed using negative, low positive and high positive controls by testing these controls in multiple repeats within the run, between the run, over different days, different lots and different operators. Mean, standard deviation and CV will be calculated. Optimization will be performed until reproducibility and precision indicates a CV % less than 10. Studies will be compared with the existing EBV ELISA assay performed in the laboratory (Diasorin, Inc). After the optimization of each antigen, all of the antigens together will be compared with ELISA testing. Internal controls and internal calibrations will be also optimized in comparison to the ELISA assay. In addition other conditions, such as incubation time, wash solution and sample dilution as well as storage conditions will be optimized.

i) Reference ranges. Reference ranges will be established through base comparison with ELISA testing. Negative specimens will be measured by ELISA and then by Luminex multiplex assay to establish reference ranges. In addition positive patient specimens will be diluted to non-detection levels to confirm established reference ranges.

j) Result Interpretation

In the IgG serology, EBV EA must be positive and should validate each reaction/assay. The control attached to bead #1 must be always negative, control attached to bead #10 must be weak negative, control attached to number #15 must be positive and control attached to #20 must be strongly positive. After all controls are positive, antibodies to either of the two new antigens: EBV encoded dUTPase and the EBV DNA encoded polymerase gene products must be positive for the test to be positive.

k) Analytical Sensitivity

Analytical sensitivity will be studied in two ways: first, positive results will be diluted to the lowest detection levels and compared to ELISA assays, and second, pooled negative specimens will be spiked with known concentration of antibodies to EBV encoded dUTPase and the EBV DNA encoded polymerase antigens and then assayed by both Luminex and ELISA.

l) Analytical Specificity

Analytical specificity will be studied by spiking pooled negative patient specimens with antibodies to EBV encoded dUTPase and the EBV DNA encoded polymerase gene product.

m) Precision

For precision six specimens will be tested. On each day of testing, each sample will be diluted twice and then loaded for four replicates resulting in a total of eight wells of each of the six samples. This protocol will be followed for three days. Selection of specimens will be done such that some of them will be clearly negative, some will be clearly positive and some will be weakly positive or just near the cutoff of the assay. These results will then be used to calculate mean U/mL values, standard deviations, and percent CV.

Summary of EBV Assay Development

A multiplex assay will be developed using specific antigens as listed above. Microsphere Luminex technology will be used for this assay. Microsphere or beads will be coated with specific antigens as listed above and then optimized and validated in singlet and multiplexes. Optimization and validation will be performed using banked human subject specimens that will be diluted to note detection to establish cutoff and reference ranges.

Method of Treatment

In another aspect, the invention provides methods of treating the EBV subset of ME/CFS patients. In some embodiments, the methods of treating a patient with CFS involves evaluating the patient for serologic evidence of the presence of nucleic acid molecules that indicate primary infection by one or more CFS-causing agents, thereby detecting the presence of each CFS-causing agent present in the patient; evaluating the patient for serologic evidence of one or more co-infection; determining whether one or more co-infections are present in the patient; administering, or causing to be administered, to a patient a therapeutically effective amount of at least one pharmaceutical composition; further comprising at least one antiviral agent such that each CFS-causing agent found in the patient is effectively treated by at least one antiviral agent administered to the patient; and, if one or more co-infections are present, also administering, or causing to be administered, to the patient therapeutically effective amount of at least one pharmaceutical composition such that each co-infection found in the patient is effectively treated by at least one pharmaceutical composition administered to the patient, thereby treating the CFS. Each pharmaceutical composition can comprise one active agent, or it can comprise a cocktail of more than one active agent. The co-infection can be with, for example, *Borrelia burgdorferi, Streptococcus pyogenes, Ehrlichia chaffeensis,*

*Babesia microti* and *Mycoplasma pneumonia*. The antiviral agent can be, for example, valacyclovir, valganciclovir, maribavir, famciclovir and foscarnet. However, any antiviral agent that is effective against a CFS-inducing infection can be used according to the methods disclosed herein.

Group A comprises CFS patients with EBV, HCMV, and/or HHV6 persistent infection in single virus or combination, but without additional co-infections. The following are the criteria for selecting these patients;
1) Patients meet international and CDC criteria for CFS and have abnormal 24 hour ECG monitors (as determined by the presence of tachycardia and/or abnormal T waves). 2) Patients are positive for HCMV, EBV and/or HHV6, as determined by detection of serum antibodies to each of these virus's or to gene products of these virus's, weather detected using enzyme-linked immunosorbent assay (ELISAN) or other methods, including those of the invention. 3) Patients are negative for CFS co-infections, such as for example *Borrelia burgdorferi, Streptococcus pyogenes, Ehrlichia chaffeensis, Babesia microti* and *Mycoplasma pneumonia*. These patient respond favorably, there are validated energy index point scores increase from less than to greater than 6, usually reaching an energy point score (EI) of 7-9 within six to twelve months antiviral therapy with appropriate antiviral agents, including, for example valacyclovir, valganciclovir, maribavir, famciclovir and foscarnet.

Group B comprises CFS patients with EBV, HCMV and/or HHV6 persistent infection, either alone or in combination, but also having one or more co-infections. The following are the criteria for group B patients;
1) Patients meet international and CDC criteria for CFS and have abnormal 24 hour ECG monitors (as determined by the presence of tachycardia and/or abnormal T waves). 2) Patients are positive for HCMV, EBV and/or HHV6 infection. 3) Patients are positive for one or more of the following: *Borrelia burgdorferi, Streptococcus pyogenes, Ehrlichia chaffeensis, Babesia microti* and *Mycoplasma pneumonia*.

CFS patients in group B can be treated with for example, valacyclovir, valganciclovir, maribavir, or other derivatives or benzimidazole, as appropriate to the particular infections present in a particular patient. famciclovir and foscarnet. CFS patients in group B can also be treated with appropriate therapy for co-infection, which may include, for example infection with *Borrelia burgdorferi, Streptococcus pyogenes, Ehrlichia chaffeensis, Babesia microti* and *Mycoplasma pneumonia*. Generally, unless group B patients are treated for the co-infection they will not improve.

Infection with *Borrelia burgdorferi* can be diagnosed by, for example, detecting the presence of IgM or IgG to *Borrelia burgdorferi* using Western blot or ELISA. It may be possible that IgG is not detected in a patient with CFS, in which case a positive IgM result would be diagnostic of infection with *Borrelia burgdorferi*. Antigens used for this assay are exact prototypes used by US Centers for Disease Control.

Infection with *Borrelia burgdorferi* can be treated with, for example, intravenous (IV) ceftriaxone 0.1-5 gm, for example 1.0-1.5 gm, intravenous piggy-back (IVPB) every 12 hours for 30 days, followed by oral amoxicillin 0.01-4.0 gm, for example 0.5-0.75 gm, 4 times/day until above serum tests negative. IV penicillin G or its equivalent every 6-8 hours can substitute for ceftriaxone. For treatment of *Borrelia burgdorferi*, as well as of any other secondary infection described herein, qualified health care personnel can prescribe appropriate dosages for effective treatment of CFS. Any dosage that falls within the scope of sound medical judgment is contemplated as part of this invention.

Adult rheumatic fever is caused by a hyperimmune response to, for example, *Streptococcus pyogenes* infection. It can be diagnosed by, for example, finding an elevated antistreptolysin O (ASO) titer (LabCorp, Dublin, Ohio); for example, an ASO titer over 400 units would be diagnostic of adult rheumatic fever or co-infection by *Streptcoccus pyogenes*. Adult rheumatic fever may also be accompanied by, for example, thickening of the aortic and/or mitral valve, which can be viewed on an echocardiogram.

Adult rheumatic fever can be treated with, for example, ceftriaxone or penicillin G as above followed by bicillin 0.1-5 Mu, for example 1.2 Mu, every 2-4 weeks until ASO titer is less than 200. A CatScan of sinuses/mastoids may be indicated to exclude obstructive sinusitis. Bicillin may be necessary for 2-4 years.

Babesiosis can be diagnosed by, for example, finding an elevated serum titer for IgG to *Babesia microti*. Chronic Babesiosis can be treated with, for example, Ataquavone 100-1500, for example 750 mg orally, plus azithromycin 0.01-4 gm, for example 0.5 gm, twice daily for 6 weeks. Detection of IgM to *Babesia microti* can also be done.

*Ehrlichia chaffeensis* co-infection can be determined by, for example, detecting a positive serum titer for IgG or IgM to *Ehrlichia chaffeensis*. Chronic Ehrlichiosis can be treated with, for example, IV doxycycline 10-1000 mg, for example 100 mg, every 12 hours for 4, 6, or 12 weeks.

Infection by *Mycoplasma pneumoniae* can be diagnosed by, for example, finding a markedly positive serum titer for IgG or IgM to *Mycoplasma pneumoniae*. Infection by *Mycoplasma pneumoniae* may also be accompanied by, for example, an abnormal standard 12-lead electrocardiogram.

*Mycoplasma pneumoniae* myocarditis can be treated with, for example, IV doxycycline plus/minus IV azithromycin for 6 weeks.

Effective sublassifications of CFS patients have not been previously recognized.

Pharmaceutical Compositions and Administration

In general, to provide a therapeutically effective amount of the antiviral agent, a suitable effective dose will be in the range of 0.1 to 20 grams a day and preferably in the range between 0.3 to 15 grams per day, more preferably about 0.5 to 10 grams per day. The dosage of course, varies with the body weight of the patient up to a 70 kg individual, a dose of 4 grams per day may be appropriate (e.g., 10 mg per KG valacyclovir every six hours). The desired dose can be presented as two—four or more smaller doses administered at appropriate intervals throughout the day. These smaller doses may be administered in unit's dosage forms. For example, for valacyclovir and famciclovir, the dosage can be, for example 14 mg/kg every 6 hours (1.0 g every 6 hours for a 70 kg person). The dosage of valacyclovir and famciclovir can be, for example, up to or at least about 0.5-8 grams every 6 hours. The dosage of valgancyclovir can be, for example, from about 450-900 mg every 12 hours, or up to or at least about 100-2000 mg or more every 12 hours, depending on for example patient weight and tolerance. For maribavir the dosage can be, for example, for about 400-500 mg every 8 hours or for example up to or at least about 100-1000 or more every 8 hours. Qualified health care personnel can prescribe appropriate dosages for effective treatment of CFS. Any dosage that falls within the scope of sound medical judgment is contemplated as part of this invention.

In particular for valacyclovir, or a derivative such valacyclovir hydrochloride, a patient can be administered a dosage in the range of 0.1 to 50 mg/kg of body weight of the patient per dosing interval, generally every 6 hours. The dosing interval is determined by the bioavailability of the antiviral agent and its excretion from the body. For example, the patient can be administered a dosage in the range of 0.3 to 40 mg/kg of body weight of valacyclovir hydrochloride orally every 6 hour. For example, a patient can be administered 10 mg/kg of body weight valacyclovir hydrochloride every 6 hours.

The treatment period for a CFS patient varies on a case-by-case basis. It is believed that for some, CFS is an ongoing and persistent problem requiring continued treatment. The duration of the therapy depends on the intensity of the CFS as affected by the therapy. One indicator of an improvement in EBV-isolated CFS patients is a decrease of a level of IgM antibodies to viral capsid antibodies (VCA) for EBV. Generally, the therapy duration is proportional to the intensity of the CFS manifestation. Accordingly, following administration of an antiviral agent, supplemental tests are helpful to check for recurrent CFS and to determine the treatment duration. The duration of treatment may be 6-18 months or longer or shorter as determined by the attending physician using the methods described herein.

Antiviral agents which demonstrate anti-herpetic action, such as those specific to, for example, EBV, HCMV, or HHV6, can be used for the treatment of chronic fatigue syndrome. Such antiviral agents may be effectively administered, for example, by oral methods, or as larger doses in time delay formulations. Included among this group of antiviral agents are valacyclovir, valganciclovir, maribavir, famciclovir and foscarnet and other herpetic antiviral agents and pharmaceutically acceptable derivatives of these antiviral agents. Such pharmaceutically acceptable derivatives include salts, hydrolysable esters and chelates of the antiviral agents and such similar derivatives which have no negative pharmaceutical effect on the patient upon administration and are thus "pharmaceutically acceptable". A pharmaceutically acceptable salt can become a for example, an acidic salt derived from an appropriate acid, for example hydrochloric, sulfuric, phosphoric, maleic, fumaric, citric, lactic, tartaric, acetic or p-toluenesulphonic acid.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method of identifying a Epstein-Barr virus (EBV) subset of Myalgic Encephalomyelitis-Chronic Fatigue Syndrome patients, the method comprising the step of:
   incubating EBV Early Antigen, Diffuse and at least one of EBV encoded DNA polymerase or EBV encoded dUTPase with a sample from a Myalgic Encephalomyelitis-Chronic Fatigue Syndrome patient, where the EBV Early Antigen, Diffuse are covalently coupled to microspheres and the at least one of EBV encoded DNA polymerase or EBV encoded dUTPase are covalently coupled to microspheres that are different from the EBV Early Antigen, Diffuse coupled microspheres;
   detecting binding of serum antibodies from the sample to the EBV Early Antigen, Diffuse and the at least one of EBV encoded DNA polymerase or EBV encoded dUTPase; and
   identifying the patient with Epstein Barr Abortive Lytic Replication when binding of the serum antibodies to the EBV Early Antigen, Diffuse and the at least one of EBV encoded DNA polymerase or EBV encoded dUTPase is detected.

2. The method of claim 1, further comprising the steps of determining an Energy Index Point Score value of the patient and obtaining the sample from the patient when the Energy Index Point Score value is 5 or less.

3. The method of claim 2, wherein the incubating step includes incubating EBV Early Antigen, Diffuse, EBV encoded DNA polymerase, and EBV encoded dUTPase with the sample, where the EBV encoded DNA polymerase are covalently coupled to microspheres that are different from the EBV Early Antigen Diffuse coupled microspheres and the EBV encoded dUTPase are covalently coupled to microspheres that are different from the EBV encoded DNA polymerase coupled microspheres and the EBV Early Antigen Diffuse coupled microspheres; the detecting step includes detecting binding of serum antibodies to the EBV Early Antigen Diffuse, the EBV encoded DNA polymerase, and the EBV encoded dUTPase; and the identifying step includes identifying the patient with Epstein Barr Abortive Lytic Replication when binding of the serum antibodies to the EBV Early Antigen Diffuse, the EBV encoded DNA polymerase, and the EBV encoded dUTPase is detected.

4. The method of claim 1, wherein the patient has an Energy Index Point Score value of 5 or less.

5. The method of claim 1, wherein the EBV Early Antigen, Diffuse coupled microspheres have a color that is different from a color of the at least one of the EBV encoded DNA polymerase or the EBV encoded dUTPase coupled microspheres.

6. The method of claim 3, wherein the EBV Early Antigen, Diffuse coupled microspheres, the EBV encoded DNA polymerase coupled microspheres, and the EBV encoded dUTPase coupled microspheres each have a color that is different from the other microspheres.

7. The method of claim 1 further comprising testing the patient for abnormal cardiac functionality, where the identifying step includes identifying the patient with Epstein Barr Abortive Lytic Replication when the patient has abnormal cardiac functionality.

8. The method of claim 1, wherein the identifying step includes identifying the patient with Epstein Barr Abortive Lytic Replication when binding of the serum antibodies to the EBV Early Antigen, Diffuse is detected at an antibody titer of 20 or more.

9. The method of claim 1, wherein the incubating step includes incubating EBV structural antigen with the sample, where the EBV structural antigen are covalently counted to microspheres that are different from the EBV Early Antigen, Diffuse coupled microspheres and the at least one of EBV encoded DNA polymerase or EBV encoded dUTPase coupled microspheres; the detecting step includes detecting binding of IgM antibodies from the sample to the EBV structural antigen; and the identifying step includes identifying the patient with Epstein Barr Abortive Lytic Replication when binding of the IgM antibodies to the EBV structural antigen is detected at an antibody titer of less than 20.

10. The method of claim 9, wherein the EBV structural antigen is at least one of EBV viral capsid antigen (VCA) or EBV VCA p18 peptide.

11. The method of claim 3, wherein the incubating step includes incubating EBV structural antigen with the sample, where the EBV structural antigen are covalently coupled microspheres that are different from the EBV Early Antigen, Diffuse coupled microspheres, the EBV encoded DNA polymerase coupled microspheres, and the EBV encoded dUTPase coupled microspheres; the detecting step includes detecting binding of IgM antibodies from the sample to the EBV structural antigen; and the identifying step includes identifying the patient with Epstein Barr Abortive Lytic Replication when binding of the IgM antibodies to the EBV structural antigen is detected at an, antibody titer of less than 20.

12. The method of claim 1, wherein the serum antibodies are IgG antibodies.

13. The method of claim 1 further comprising the step of treating the patient identified as having Epstein Barr Abortive Lytic Replication with an antiviral agent.

14. The method of claim 13, wherein the antiviral agent is an antiviral nucleoside.

15. The method of claim 13, wherein the antiviral agent is one or more of valacyclovir, valganciclovir, maribavir, famciclovir, or foscarnet.

* * * * *